United States Patent

Stackhouse et al.

[11] Patent Number: 4,986,282
[45] Date of Patent: Jan. 22, 1991

[54] FACE SHIELD SYSTEM

[76] Inventors: Wyman H. Stackhouse, 3201 Poinsettia Ave., Manhattan Beach, Calif. 90266; Ian M. Williamson, 555 N. Harbor Dr., Redondo Beach, Calif. 90277

[21] Appl. No.: 94,712

[22] Filed: Sep. 9, 1987

[51] Int. Cl.⁵ .................. A61F 11/00; A61F 9/00; A42B 1/06
[52] U.S. Cl. .................. 128/857; 128/858; 2/410
[58] Field of Search .................. 2/8, 9, 10, 12, 410; 128/100, 205.25, 206.12, 206.21, 206.27, 207.11, 857, 858

[56] References Cited

U.S. PATENT DOCUMENTS

| | | | |
|---|---|---|---|
| 2,194,492 | 3/1940 | Bowers | 2/8 |
| 2,272,833 | 2/1942 | Dockson | 2/8 |
| 2,729,820 | 1/1956 | Anderson | 2/9 |
| 2,788,558 | 4/1957 | Bowers, Jr. | 2/8 |
| 3,041,622 | 7/1962 | Gurtowski | 2/8 |
| 3,555,562 | 1/1971 | Patton, Jr. | 2/10 |
| 3,696,442 | 10/1972 | Amundsen et al. | 2/8 |
| 4,630,317 | 12/1986 | Brown et al. | 2/12 |

*Primary Examiner*—Robert A. Hafer
*Assistant Examiner*—Michael Brown
*Attorney, Agent, or Firm*—Singer & Singer

[57] ABSTRACT

There is herein described an improved anti-infection shield system designed for the protection of all health care workers from accidental exposure to body fluids from virus infected patients whereby an ultra-light face shield protects the eyes, nose and oral cavity from inadvertent splashing of patient blood or other body fluids, the shield being very light in weight, optically clear, and readily replaceable.

4 Claims, 2 Drawing Sheets

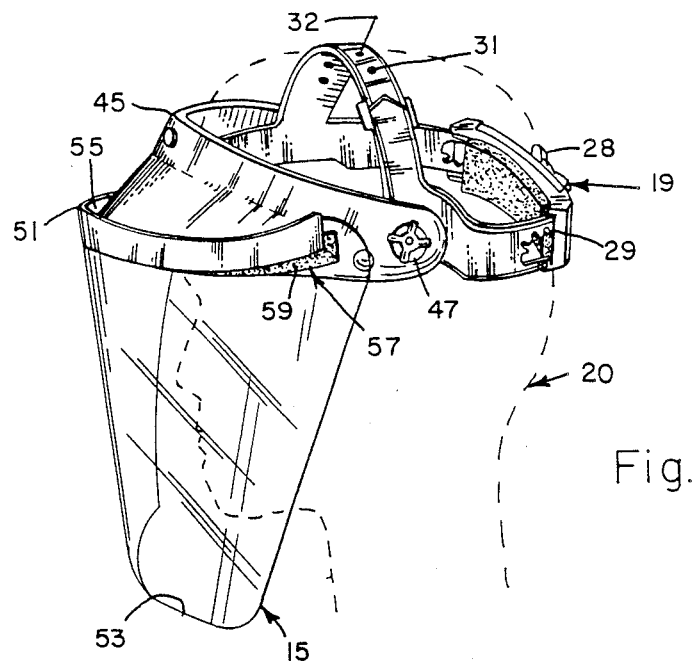
Fig. 1.
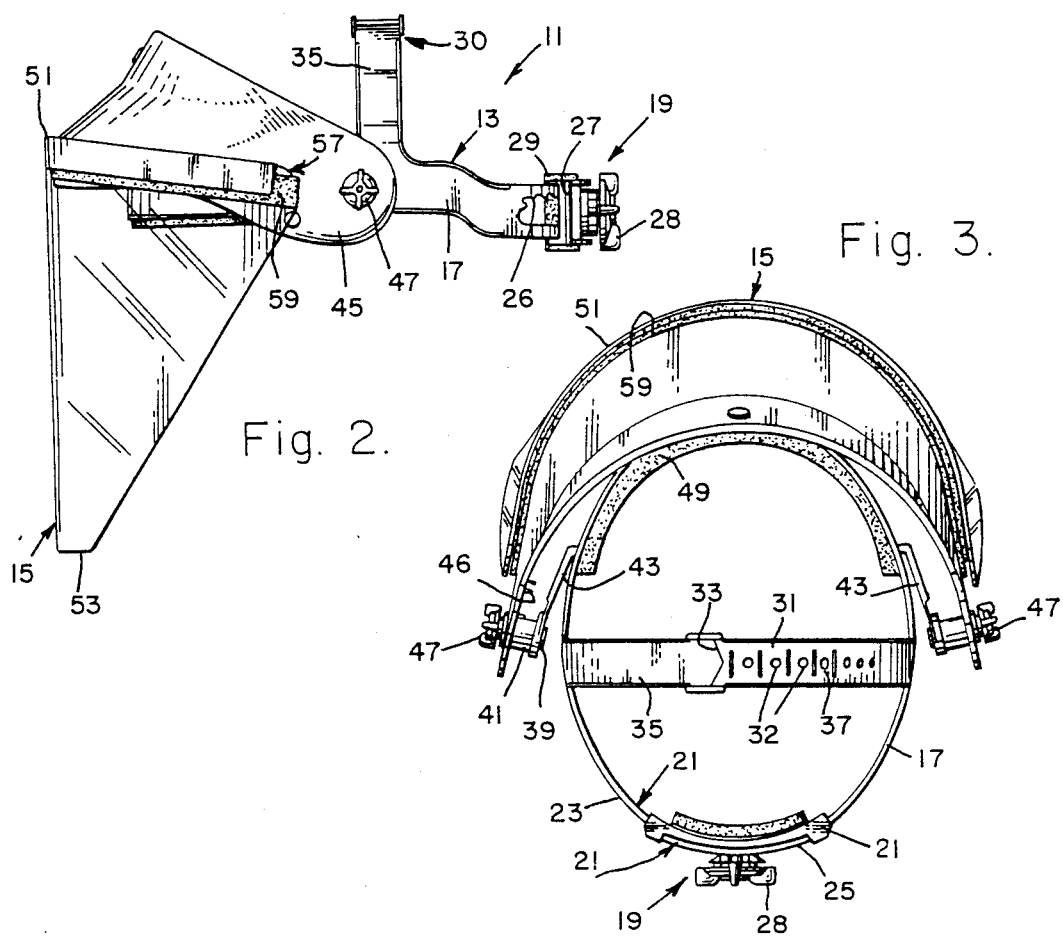
Fig. 2.
Fig. 3.

FACE SHIELD SYSTEM

TECHNICAL FIELD

This invention relates to the field of masking systems designed to protect the user's face from foreign and dangerous contaminants while allowing the user full freedom of the use of his or her hands. More specifically, the invention relates to such face plates designed for the protection of health car workers from accidental contamination from liquid-carried viruses.

BACKGROUND ART

Helmets or masks used in the medical field have heretofore been primarily designed to maintain certain work areas free from contaminating particulate. In the field of medicine, for example, the medical profession has been plagued for many years with the problem of post-operative infection resulting from contamination of open wounds during surgery. This problem has basically been solved by providing an evacuation system incorporated in the helmet which exhausts through a filter so that contaminating particles such as hair, skin cells, make-up, and the like, originating in the helmet do not reach the clean room environment.

In the last few years, however, a new problem has been recognized with respect to the medical facility environment. The problem is with relatively new viruses which may expose medical personnel merely by being splattered by blood o other body fluids from a person carrying the virus. That is, the medical worker must be protected from any contaminated fluid that may enter his or her eyes, nose, and oral cavity, while providing the worker with unobstructed vision. At the same time, it is necessary that the any splattered portion of the protective device be readily replaceable by an non contaminated counterpart.

In the prior art related to face masks used in the medical area, several designs have been developed. For example, in U.S. Pat. No. 3,955,570, there is described a surgical exhaust mask having a support member designed to fit the head of a wearer and that supports a generally spherically configured face plate that is secured at both its upper side and lower center portions to a fixed portion of the support member. Thus, the face plate is relatively difficult to remove and replace and is not tiltable to temporarily swing upwardly away from a position adjacent the wearer's face so as to provide facial access when a brow needs to be wiped, etc.

The prior art is also exemplified by U.S. Pat. No. 3,529,594, which discloses an article of protective clothing including a mask having a fixed rectangular transparent window rigidly attached to an adjustable head band arrangement.

These examples of the prior art are primarily concerned with the problem of preventing air containing particles of dust, hair, lint, and the like, from entering a clean operating room environment. There was no concern in these designs with the protection of health care workers from accidental exposure to body fluids from virus infected patients. It should therefore be clear that an anti-infection face shield system that provides for a quick release and replacement of a tiltable transparent face shield would constitute a significant advancement in the art.

In accordance with the present invention, an improved anti-infection face shield system for full face protection system is provided whereby the possible problems heretofore alluded to in general medical and especially in surgical environments utilizing standard masking means are substantially eliminated. That is, the invention provides an advantageous means to preclude contamination of all health care workers from accidental exposure to body fluids from virus infected patients.

SUMMARY OF THE INVENTION

In view of the foregoing factors and conditions characteristic of the prior art, it is a primary object of the present invention to provide a new and improved anti-infection face shield system for all health care workers.

Another object of the present invention is to provide a relatively simple yet effective anti-infection face shield system that prevents health care workers from being exposed to body fluids from virus infected patients.

Still another object of the present invention is to provide a unique disposable anti-infection face shield that is less restricting than goggles which protect only the users eyes.

Yet another object of the present invention is to provide an ultra light weight and readily disposable anti-infection face shield which protects the eyes, nose, and oral cavity from inadvertent splashing of patient blood or other body fluids.

In accordance with an embodiment of the present invention, an anti-infection face shield system which protects the eyes, nose and oral cavity from inadvertent splashing of patient blood or other body fluids includes a support member adjustably sized and shaped to fit the head of the user and includes a generally horizontal head band and an upper cross band section as an integral part of the support member. A curved visor member is positioned adjacent the forward portion of the support member and adjustably attached at its opposite ends to associated positions on the sides of the support member. A curved transparent face shield is provided having an upper peripheral portion conformable generally to the curved lower peripheral portion of the visor member and extending therebelow to protect the user's face from splashed fluids when the face shield is in its normal generally vertical position. And disposed on the outer surface of the lower peripheral portion of the visor member and on the inner surface of the upper peripheral portion of the face shield is a quick release/attachment means for releasably attaching the face shield to the visor member and to function as a quick release mechanism.

Both the horizontal and vertical portions of the support member may be provided with adjustment mechanisms to readily adapt the face shield system to conform to the size and shape of any user's head. Also, the visor member may include a detent mechanism to allow dependable tilt positioning of the face shield.

The features of the present invention which are believed to be novel are set forth with particularity in the appended claims. The present invention, both as to its organization and manner of operation and use, together with further objects and advantages thereof, may best be understood by making reference to the following description taken in conjunction with the accompanying drawings in which like reference characters refer to like elements in the several views.

BRIEF DESCRIPTION OF THE DRAWINGS

FIG. 1 is a perspective view of the anti-infection face shield system according to the invention;

FIG. 2 is a side elevational view of the face shield system of FIG. 1;

FIG. 3 is a top plan view of the face shield system of FIG. 1;

DESCRIPTION OF THE PREFERRED EMBODIMENT

Figure 4:
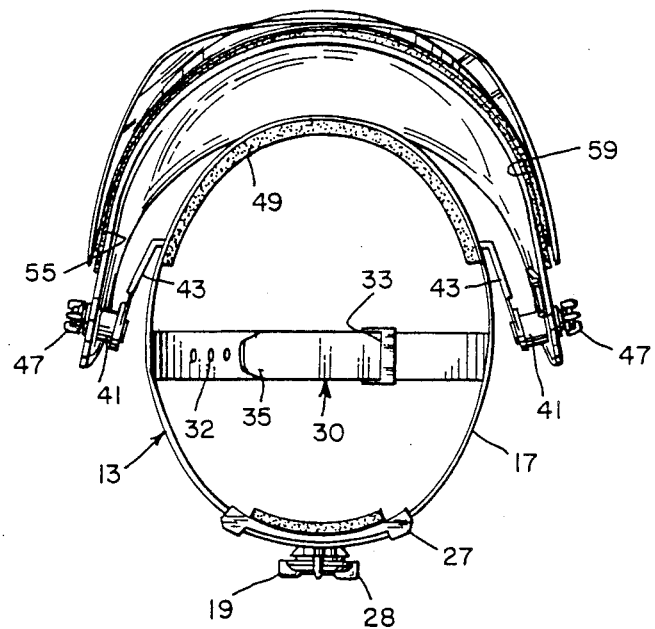
FIG. 4 is a bottom plan view of the face shield system of FIG. 1.
Figure 5:
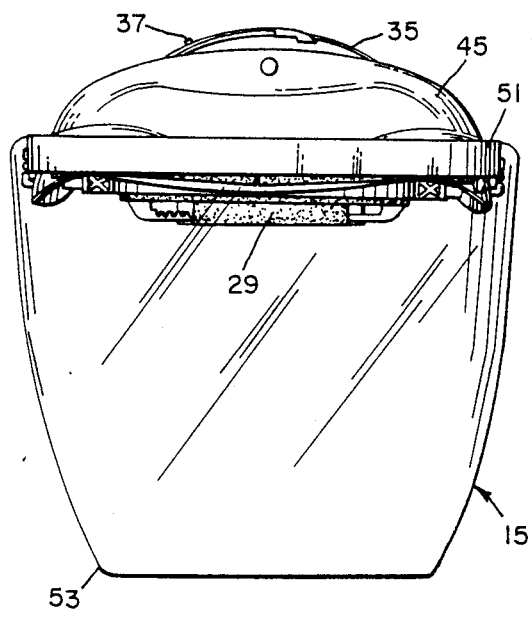
FIG. 5 is a front elevational view of the shield system of FIG. 1.
Figure 6:
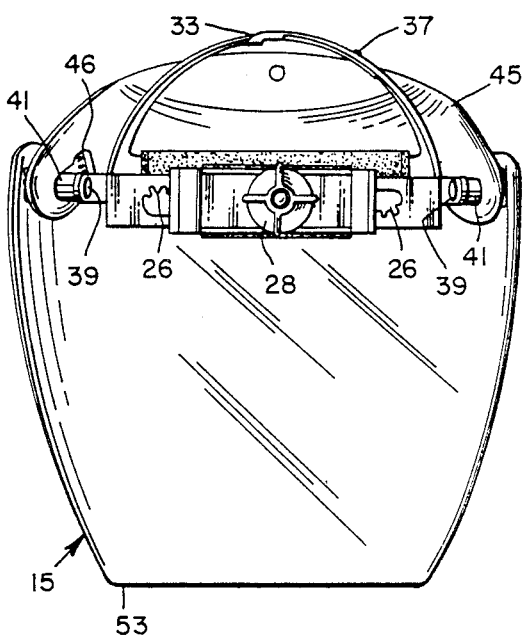
FIG. 6 is a rear elevational view of the anti-infection face shield system as shown in FIG. 1.

Referring now to the drawings and more particularly to FIG. 1, there is shown an anti-infection face shield 11 system in accordance with a presently preferred embodiment of the present invention. The face shield system 11 includes at least a semirigid frame 13 to which an ultra-light full face, optically clear polycarbonte face shield 15 is readily removably attached.

The frame 13 includes a head band portion 17 with an adjustable rear section 19 so that the size of the head band can be readily altered to accommodate the dimensions of any user's head (see dashed outline 20). The adjustable rear section 19 may include overlapping end straps or cross bands 21. The two free ends 23 and 25 of the straps 21 are provided with suitable ratchet formations 26 and slide in overlapping relation within a housing 27. A knob 28 has an appropriate pinion configuration within the housing to engage the straps and retract or extend them.

For comfort, a cushion 29 may be adhesively attached to the inner surface of the housing 27, which cushion may be fabricated from any soft material such as a foam plastic or rubber, for example. Preferably, integral with the head band portion 17 is an upper cross band section 30 including a free end portion 31 having plurality of apertures 32 and an end loop 33. The other free end portion 35 is slidably mounted in the loop 33 and is formed with a boss 37 which may be snapped into any one of the apertures 32 to provide a desired band length.

Pivotally attached by threaded posts 39, which are mounted on spacer posts 41 carried by arms 43 attached to the sides of the head band portion 17, is a relatively stiff or rigid visor 45. The visor ca be adjustably fixed at any desired position that may be defined, for example, by a conventional detent assembly 46 by simply tightening knobs 47 threaddably attached to an associated one of the posts 39. Similar to the rear pad or cushion 29, a forehead cushion or pad 49 may be adhesively or otherwise attached to the forward section of the head band portion 17.

The full face shield 15 is preferably contoured to be wider at its upper portion 51 than at its lower portion 53, and the shield also is provided with a first segment or strip 55 of a quick release shield-retaining mechanism 57. The segment or strip 55 is permanently attached by any conventional means such as an adhesive to the inner surface of the aforesaid upper edge portion 51 of the shield, while an associated second segment or strip 59 of the quick release retaining mechanism 57 is permanently attached to the outer lower front surface of the visor 45. The quick release retaining mechanism 57 may be fabricated of any conventional material known for these properties such as, for example, any conventional loop and hook fabrication, as is well known in the art. This advantageous feature allows the shield 15 to be easily and quickly pulled free of the visor 45 and as easily and quickly replaced by another such shield having a first segment or strip 55

From the foregoing it should be evident that there has herein been described a new and improved anti-infection face shield system for all health workers which is relatively simple yet effective to prevent health care workers from being exposed to body fluids from virus infected patients. As noted, the invention further provides a unique disposable anti-infection face shield that is less restricting than goggles which protect only the users eyes, and one that is ultra light in weight.

Although the invention has been described in detail with respect to presently preferred embodiments of the invention, it should be understood that the invention may be practiced using similar functioning but different elements, under the scope of the appended claims.

What is claimed is:

1. A face shield system for protection of health care workers from accidental exposure to the body fluids from virus infected patients, comprising:
    a support member adjustably sized and shaped to fit the head of the user and including a generally horizontal head band and an upper cross band section as an integral part of said support member;
    a curved face shield having an upper peripheral portion conformable generally to the curved lower peripheral portion of said support member and extending therebelow to protect the user's face from splashed fluids when said face shield is in its normal generally vertical position; and
    a hook and pile engaging and holding means disposed on the outer surface of said lower peripheral portion of said support member and on the inner surface of said upper peripheral portion of said face shield for frictionally engaging and holding said face shield to said support member thereby providing a quick release mechanism for separating said face shield from said support member.

2. The face shield system according to claim 1, wherein said generally horizontal head band and said upper cross band sections include adjustable arrangements.

3. The face shield system according to claim 2, wherein said adjustable mechanism associated with said generally horizontal head band includes a ratchet mechanism whereby only one hand of the user is required to change the size of said head band.

4. The face shield system according to claim 1, where said hook and pile engaging and holding means includes a loop structure and a cooperating hook structure, a different one for each of said structures being disposed on the outer surface of said lower peripheral portion of said support member and on the inner surface of said upper peripheral portion of said face shield.

* * * * *